United States Patent
Chitale et al.

(10) Patent No.: US 6,646,437 B1
(45) Date of Patent: Nov. 11, 2003

(54) SYSTEM AND METHOD FOR CLAY TYPING USING NMR-BASED POROSITY MODELING

(75) Inventors: Dattatraya V. Chitale, Houston, TX (US); George R. Coates, Three Rivers, CA (US); Peter Ian Day, Houston, TX (US); Richard F. Sigal, Spring, TX (US)

(73) Assignee: Halliburton Energy Services, Inc., Houston, TX (US)

(*) Notice: Subject to any disclaimer, the term of this patent is extended or adjusted under 35 U.S.C. 154(b) by 10 days.

(21) Appl. No.: 09/827,835

(22) Filed: Apr. 6, 2001

Related U.S. Application Data
(60) Provisional application No. 60/195,527, filed on Apr. 7, 2000.

(51) Int. Cl.[7] .................................................. G01V 3/00
(52) U.S. Cl. .................................................. 324/303; 702/8
(58) Field of Search .................... 324/303; 702/6–13; 703/2–10; 73/152

(56) References Cited

U.S. PATENT DOCUMENTS

| | | | | |
|---|---|---|---|---|
| 3,638,484 A | * | 2/1972 | Tixier | 73/152.02 |
| 4,095,102 A | * | 6/1978 | Tixier | 250/265 |
| 4,495,604 A | * | 1/1985 | Clavier et al. | 367/25 |
| 4,502,121 A | * | 2/1985 | Clavier et al. | 702/13 |
| 4,622,849 A | * | 11/1986 | Fertl | 73/152.14 |
| 4,710,713 A | | 12/1987 | Taicher et al. | 324/303 |
| 4,717,876 A | | 1/1988 | Masi et al. | 324/303 |
| 4,717,877 A | | 1/1988 | Taicher et al. | 324/303 |
| 4,717,878 A | | 1/1988 | Taicher et al. | 324/303 |
| 4,953,399 A | * | 9/1990 | Fertl et al. | 73/152.02 |
| 5,055,787 A | | 10/1991 | Kleinberg et al. | 324/303 |
| 5,055,788 A | | 10/1991 | Kleinberg et al. | 324/303 |
| 5,146,086 A | * | 9/1992 | De et al. | 250/253 |
| 5,212,447 A | | 5/1993 | Paltiel | 324/300 |
| 5,280,243 A | | 1/1994 | Miller | 324/303 |
| 5,309,098 A | | 5/1994 | Coates et al. | 324/303 |
| 5,412,320 A | | 5/1995 | Coates | 324/303 |
| 5,469,062 A | * | 11/1995 | Meyer, Jr. | 324/338 |
| 5,498,960 A | * | 3/1996 | Vinegar et al. | 324/303 |
| 5,517,115 A | | 5/1996 | Prammer | 324/303 |
| 5,557,200 A | | 9/1996 | Coates | 324/303 |
| 5,668,369 A | * | 9/1997 | Oraby | 250/269.5 |
| 5,675,147 A | * | 10/1997 | Ekstrom et al. | 250/256 |
| 5,696,448 A | | 12/1997 | Coates et al. | 324/303 |
| 5,862,513 A | * | 1/1999 | Mezzatesta et al. | 702/9 |
| 5,936,405 A | | 8/1999 | Prammer et al. | 324/303 |
| 5,992,228 A | * | 11/1999 | Dunham | 73/152.05 |
| 6,005,389 A | | 12/1999 | Prammer | 324/303 |
| 6,023,164 A | | 2/2000 | Prammer | 324/303 |
| 6,032,101 A | * | 2/2000 | Freedman et al. | 702/8 |
| 6,052,649 A | * | 4/2000 | Goldman et al. | 702/11 |
| 6,109,368 A | * | 8/2000 | Goldman et al. | 175/39 |

(List continued on next page.)

OTHER PUBLICATIONS

Miller et al., "Spin Echo Magnetic Resonance Logging: Porosity and Free Fluid Index Determination," *Society of Petroleum Engineers*, SPE 20561 (1990), pp. 321–334.

*Primary Examiner*—Louis Arana
*Assistant Examiner*—Dixomara Vargas
(74) *Attorney, Agent, or Firm*—Pennie & Edmonds

(57) ABSTRACT

System and method for characterizing formation properties based on NMR measurements. NMR clay measurements of this invention distinguish between interstitial pore water and the water adsorbed by the clay minerals. The measurements can be used to determine the quantity of adsorbed water in different clays and correct previously available data obtained using conventional density and neutron porosity logs. A new petrophysical parameter wetness clay is defined as an intrinsic parameter for clays, and its value is computed for members of the smectite group of clays, such as montmorillonite. The wet clay values for the density, neutron logs based on the adsorbed water in clays are used to enhance the quality and accuracy of the overall log interpretation.

27 Claims, 11 Drawing Sheets

U.S. PATENT DOCUMENTS

| | | | |
|---|---|---|---|
| 6,147,489 A | * 11/2000 | Freedman et al. | 324/303 |
| 6,229,308 B1 | * 5/2001 | Freedman | 324/303 |
| 6,337,568 B1 | * 1/2002 | Tutunji et al. | 324/303 |
| 6,366,087 B1 | * 4/2002 | Coates et al. | 324/303 |
| 6,377,042 B1 | * 4/2002 | Menger et al. | 324/303 |
| 6,408,953 B1 | * 6/2002 | Goldman et al. | 175/39 |
| 6,424,919 B1 | * 7/2002 | Moran et al. | 702/6 |
| 6,470,274 B1 | * 10/2002 | Mollison et al. | 702/7 |

* cited by examiner

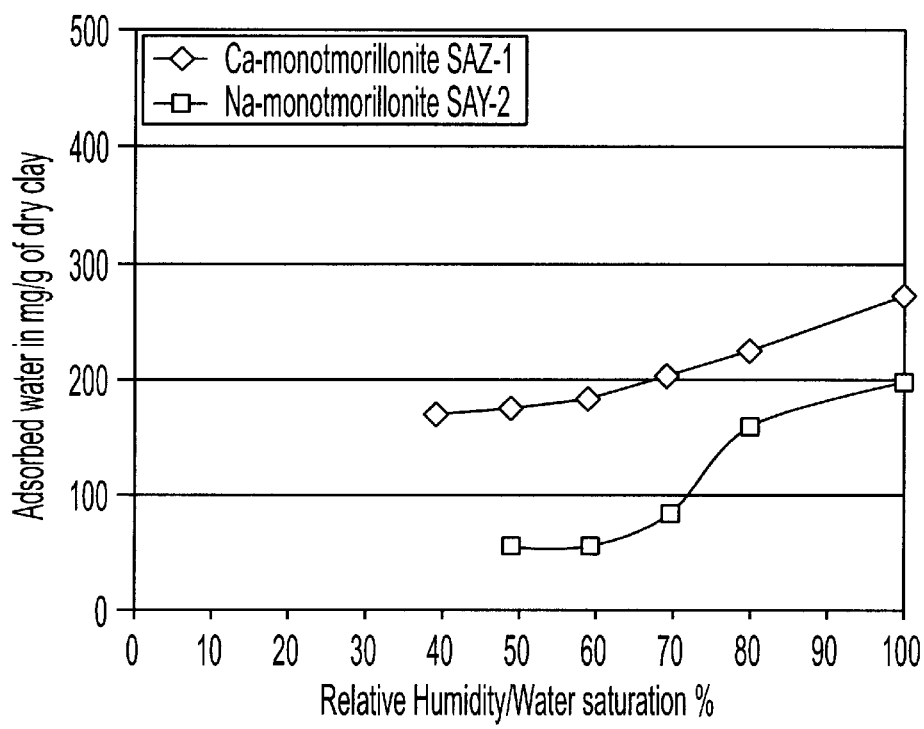

Fig. 3

Table 1: Amount of water adsorbed by montmorillonites upon hydration by water vapors. Data from various published adsorption isotherms.

| Type of clay | water adwsorbed in mg/g of dry clay | Authors of the published data |
|---|---|---|
| Na-montmorillonite | 400 | Mooney et. al. (1952) |
| | 365 | Bush & Jenkins (1968) |
| | 200 | Calvert (1972) |
| | 250 | Johnston et. al. (1992) |
| | 324 | Berend et.al. (1995) |
| | 275 | Johnston et.al. (1999) |
| | 198 | Chitale et.al. (1999) |
| Ca-montmorillonite | 250 | White & Pichla (1959) |
| | 270 | Calvert (1972) |
| | 400 | Johnston et.al. (1992) |
| | 275 | Prost et. al. (1998) |
| | 350 | Xu & Johnston (1999) |
| | 270 | Chitale et.al. (1999) |

Fig. 3A

SYSTEM AND METHOD FOR CLAY TYPING USING NMR-BASED POROSITY MODELING

The present application claims priority from provisional application Ser. No. 60/195,527 filed Apr. 7, 2000.

FIELD OF THE INVENTION

The present invention generally relates to formation analysis and more particularly to identifying clay types and properties based on NMR porosity measurements using user-adjusted modeling parameters.

BACKGROUND OF THE INVENTION

The ability to differentiate between fluid types is one of the main concerns in the examination of the petrophysical properties of a geologic formation. For example, in the search for oil it is important to separate signals due to producible hydrocarbons from bound ones, as well as from the signal contribution of brine, which is a fluid phase of little interest. Extremely valuable is also the capability to distinguish among clay-bound water, capillary-bound water, movable water, gas, light oil, medium oil, and heavy oil.

In this regard, it is desirable to understand the structure and properties of the geological formation. A significant aid in this evaluation is the use of wireline logging and/or logging-while-drilling (LWD) measurements of the formation surrounding a borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

The hydrocarbon production potential of a subsurface formation is described in terms of a set of "petrophysical properties." Such properties may include the lithology or the rock type, e.g., amount of sand, shale, limestone, or more detailed mineralogical description; the porosity or fraction of the rock that is void or pore space; the fluid saturations or fractions of the pore space occupied by oil, water and gas, and others. Wireline logging tools do not directly measure petrophysical properties, they measure "log properties", for example, bulk density, electrical resistivity, acoustic velocity, or nuclear magnetic resonance (NMR) decay. Log properties are related to the petrophysical properties via mathematical or statistical relations, which are generally known in the art. In practice, frequently several different logging tools are combined and used simultaneously to obtain an integrated set of measurements. Thus, different tools may be used to obtain information about the same set of formation properties using different techniques, or different tools may be used to obtain information about different formation properties. In order to make optimal use of the measurement results from different tools, in practice their responses to known formations are modeled and, the model responses are compared to actual logs. The error signal generated in the process serves to improve the parameter estimates of the models and ultimately to provide an understanding of the petrophysical properties of the formation.

Several approaches have been proposed in the past to model the structure of geological formations, as well as the ability of different structures to retain fluids. Such models can be extremely valuable in practice. The present application discloses a new and improved nuclear magnetic resonance (NMR) porosity model using adsorbed water content in clay minerals. The proposed model can be used among other purposes for clay typing in formation evaluation.

NMR logging has proved very useful in formation evaluation. NMR logging tools known in the art include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL ® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115; 5,557,200; 5,696,448; 5,936,405, 6,005,389 and 6,023,164. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992. The content of the above patents is hereby expressly incorporated by reference for all purposes, and all non-patent references are incorporated by reference for background.

Technology advances have made it possible to reduce the inter echo spacing of the downhole NMR logging tools such that these tools are able to measure very fast (for example, less than 1 ms) relaxing components of the subsurface rocks. See Prammer et.al., (1996). In most cases, these fast $T_2$ relaxation times are ascribed to the water bound in the clay mineral component of the rocks. As a result, the petroleum industry's interest in the application of NMR technology to aid in shaly sand evaluation has grown considerably. With reference to the list provided at the end of this section, useful prior art includes the publications by Prammer et. al., (1996); Allen et. al., (1998); Matteson et. al., 1998; Chitale et. al., (1999). However, until recently it remained unclear whether or not the water adsorbed on the clay surface (the so called clay-bound water in petrophysics) is detectable by NMR. This paper presents results of a systematic laboratory NMR characterization of pure montmorillonite clay with an objective to clearly document the NMR signature of the water adsorbed on the clay surface. This will help establish a physical basis for the application of NMR in shaly sand formation evaluation.

NMR relaxometry experiments on clays and clayey rocks have shown that the adsorbed water on the surface of clays (or the so called clay-bound water in petrophysics) is fully represented in the NMR $T_2$ distribution. Accordingly, it is desirable to provide NMR characterization of different clays for use in the interpretation of nuclear (i.e., density & thermal neutron) and NMR porosity logs acquired from shaly sand reservoirs.

Cross plots, overlays and modeling of the log responses with respect to the formation lithology are common techniques in the evaluation of density and neutron porosity logs. Bulk density and neutron porosity values for wet and dry clays are required inputs for such evaluation. Compilations of nuclear logging parameters for various sedimentary minerals, including those for wet- and dry clay minerals have been published in the prior art. See, Edmundson and Raymer, (1979), Ellis et. al., (1994), and wireline logging service companies, such as Halliburton, (1991) and Schlumberger, (1994). Bulk density and neutron porosity values for water-wet montmorillonites published in these compilations are based upon chemical analyses of the clay or theoretical derivations of chemical formulae that include certain fixed number of water molecules per unit cell of montmorillonite. In one aspect, the methods of this invention are used to refine the above wet-clay parameters based on new insights obtained from an NMR study of the physical characteristics of the adsorbed water on montmorillonite surface.

NMR characterization of clays, and more specifically montmorillonites, combined with other spectroscopic data (Touret et. al., 1990) can offer petrophysically meaningful values for the quantity of water associated with montmorillonite occurring in the sedimentary rocks. Deeper understanding of the mechanism of water retention by clays, such as montmorillonite, and of the geometry of the space occupied by the clay-bound water provide a physical basis to quantify the adsorbed water in clays irrespective of their mode of occurrence or morphology, and therefore is desirable in practice.

Details of the methods and techniques in accordance with the present invention are provided below. The interested reader is directed for additional background information to the disclosure of the following references, which are incorporated herein by reference for background. For simplicity, in the following disclosure only the first author and year of publication are provided.

REFERENCES

Berend, I., Cases, J. M., Francois, M., Uriot, J. P., Michot, L., Masion, A., and Thomas, F. (1995) "Mechanism of adsorption and desorption of water vapor by homoionic montmorillonites:2: The Li, Na, K, and Cs exchangeable forms": Clays and Clay Minerals, 43, p. 324–364.

Chitale, D. V., Day, P. I. and Coates, G. R. (1999) "Petrophysical significance of Laboratory NMR and Petrographic Investigation on a Shaly-sand Core": SPE 56765 Presented at the 1999 SPE-ATCE, Houston, October 3–6, 5 p.

Edmundson, H. and Raymer, L. L. (1979) "Radioactive logging parameters for common minerals": Presented at the 20th Annual Symposium of the SPWLA, June 3–6, paper O, p.1–20.

Ellis, D., Howard, J., Flaum, C., McKeon, D., Scott, H., Serra, O. and Simmons, G. (1994) "Mineral logging parameters: Nuclear and acoustic": Petrophysics, SPE Reprints Series No.39, p. 52–66.

Grim, R. E. (1968) "Clay Mineralogy, 2nd Ed.": McGraw Hill Book Co., New York, p.250–270.

Guven, N., (1992) "Molecular Aspects of Clay Water Interactions" in Clay-Water Interface and its Rheological Implications; CMS Workshop Lectures, Volume 4; N. Guven and R. M. Pollastro Editors, p. 2–79.

Halliburton Logging Services Log Interpretation Charts (1991), p. APP4a.

Johnston, C. T., Sposito, G., and Erickson, C. (1992) "Vibrational probe studies of water interactions with montmotillonite": Clays and Clay Minerals, 50, p.722–730.

Low, P. F. (1980) "The swelling of clay: II. Montmorillonites": Soil Sci. Soc. Amer. J., 44, p. 667–676.

Prost, R. (1976) "Interactions between adsorbed water molecules and the structures of clay minerals": Hydration mechanisms of smectites: in Proc. Intl. Clay Conf. 1975, S. W. Bailey, ed., Applied Publishing Ltd., Wilmette, Ill., p. 351–360.

Prost, R., Koutit, T., Benchara, A., and Huard, E. (1998) "State and location of water adsorbed on clay minerals: Consequences of the hydration and swelling—shrinkage phenomena": Clays & Clay Minerals, 46, p. 117–131.

Schlumberger Log Interpretation Charts (1994), p. B-6.

Sposito, G. and Prost, R. (1982) "Structure of water adsorbed in smectites": Chem. Rev., 82, p. 553–573.

Touret, O., Pons, C. H., Tessier, D. and Tardy, Y. (1990) "Etude de la repartition de l'eau dans des argiles sature'es Mg 2+ aux fortes teneurs en eau": Clay Minerals, 25, p. 217–234.

Van Olphen, H. (1965) "Thermodynamics of interlayer adsorption of water in clays: Sodium vermicullite": J. Colloidal Sci., 20, p. 822–837.

SUMMARY OF THE INVENTION

The limitations of current formation evaluation techniques outlined above are addressed by the present invention, which derives a set of clay parameters and uses these parameters along with measured logs and knowledge of the associated tool response models to provide improved estimates of the properties of clay materials and other earth formation attributes.

The invention is based in part on the determination that adsorbed water on the surface of water-saturated clays, such as montmorillonites, (the so-called clay-bound water in petrophysics) is fully represented in the NMR $T_2$ distribution. This determination finds support in the good match between the NMR-measured and the actual water content of wet clays. In such clays the surfacially adsorbed water is found to coexist with the water occupying the inter-aggregate clay pores, analogous to the condition of water-wet sedimentary clays in the subsurface. These observations further confirm the suitability of NMR techniques for total porosity measurement.

Experiments confirmed that the NMR methods in one aspect of this invention are capable of detecting the adsorbed water on the clay surface even when that is the only form of water present. For montmorillonite this phase of water almost entirely resides on the internal surface of the clay, whose geometry does not change within the hydrated clay. Hence, it was observed that the NMR $T_2$ distributions obtained from these clays are uni-modal. In addition, it was observed that the $T_2$ relaxation is linearly related to the volume of water of hydration V and surface S in accordance with the relationship: $1/T_2 = pS/V$.

In another aspect of the invention, it was observed that NMR $T_2$ distributions obtained from clays, such as water-saturated montmorillonites, are bi-modal because they represent water relaxing in pore spaces with two different geometries. Faster $T_2$ times, which for montmorillonite cluster around 1 ms, are a measure of the water in the hydration shells of exchangeable cations in the interlamellar space of clays. The $T_2$ times slower than 1 ms, on the other hand, represent water relaxing in the inter-aggregate pores of the water-saturated clays. Extrapolation of the hydration data and the NMR $T_2$ distribution combined with the other published spectroscopic data suggest that the water adsorbed on the clay surface in water-saturated montmorillonites amounts to about 500 mg per dry g of clay.

Accordingly, in one aspect of this invention, the use of NMR offers a new approach to differentiating between the surficially adsorbed water in clays, such as montmorillonite, from the interstitial pore water in rocks. As noted, NMR characterization suggests that the threshold level of adsorbed water in this clay is 500 mg/g of dry clay. This parameter is believed to be an intrinsic property of water-wet montmorillonite. A new characteristic parameter, called wetness-clay, is proposed in accordance with the present invention and is defined as the ratio of volume of adsorbed water divided by the volume of wet clay. This parameter constitutes an intrinsic property of clays, and its computed value for montmorillonite is 0.57.

Based on the NMR methods of this invention, the wet clay bulk density values for clays can be corrected. For example based on the NMR measurements, the 2.12 g/cc value prevalent in the literature on log interpretation for montmorillonite has been revised. The wet clay density computed in accordance with this invention for montmorillonite is 1.7 g/cc, which value translates to an apparent porosity of 58% for a standard sandstone matrix. Further, it is proposed to refine the thermal neutron porosity log parameter for water-wet montmorillonite to 70%, considering that the neutron porosity is a composite bulk response from water as also the hydroxyls in clays.

Based on sedimentary petrological considerations and the NMR $T_2$ characteristics of the water-saturated montmorillonites it is postulated that the above values of wetness, bulk density and thermal neutron porosity for this clay remain constant unless the clay undergoes mineralogical transformation.

In another aspect, the present invention makes use of the concept of the wetness clay parameter designating the fraction of the characteristic volume of adsorbed water in a given clay mineral, which is proportional to the volume of that clay mineral. An NMR porosity model using the characteristic wetness values for various clay minerals is then applied in a method of clay typing primarily for use in shaly sand log analysis. The system and method in this aspect of the invention is based on constrained inversion of a completely determined or overdetermined log data set comprising gamma (GR), bulk density (Rhob) and thermal neutron (Nphi) and NMR logs. These logs have well defined linear responses proportional to the volumetric components of matrix minerals, clay minerals and pore fluids. Using the proposed NMR porosity model one can derive a generic log, which accurately reflects the properties of various clay types.

In particular, in one aspect the invention is a nuclear magnetic resonance (NMR) method for differentiating between adsorbed water and interstitial water content in a clay material, comprising: (a) successively passing the clay material through controlled levels of hydration; (b) performing an NMR experiment on the clay material at each of the controlled levels of hydration; (c) computing $T_2$ relaxation distributions from NMR signals obtained in each experiment; (d) determining the minimum level of hydration of the clay material at which $T_2$ relaxation distribution becomes bi-modal; and (e) computing a measure of adsorbed water in the clay material based on the determined minimum level of hydration.

In specific embodiments the method further comprising one or more of the steps of: computing a measure of the interstitial water content in the clay material based on slow $T_2$ relaxation components in a bi-modal relaxation distribution; repeating steps (a) through (e) for a different clay material; providing a listing of the computed measures of adsorbed water for each different clay material; comparing values of the computed measures of adsorbed water for each different clay material to a corresponding value for such material obtained without the use of NMR experiments; and computing a correction of the value of adsorbed water for a clay material obtained without the use of NMR experiments based on the corresponding value obtained in step (e).

In another aspect, the invention is a method for determining petrophysical properties of geologic formations containing clay materials, comprising: (a) providing a model of the geologic formation, said model comprising a wetness parameter for that fraction of the characteristic volume of adsorbed water in a given mineralogy component, which is proportional to the volume Vclay of that component; (b) providing log data corresponding to the geologic formation; (c) performing constrained inversion of the provided data log using the model of the geologic formation; and (d) determining petrophysical properties of geologic formations based on the provided model and the performed constrained inversion. In a preferred embodiment the method uses at least NMR log data, and at least one of the group of gamma, bulk density and thermal neutron log data.

In another aspect, the invention is a geological formation interpretation system comprising: means for providing a model of a geologic formation, said model comprising a wetness parameter for that fraction of the characteristic volume of adsorbed water in a given mineralogy component, which is proportional to the volume Vclay of that component; means for providing log data corresponding to the geologic formation; processor means performing constrained inversion of the provided data log using the model of the geologic formation; and means for determining petrophysical properties of geologic formations based on the provided model and the performed constrained inversion.

In yet another aspect, the invention is a geological formation interpretation system comprising a specially programmed computer having: a first memory for storing a plurality of measurement logs of a geological formation; a second memory for storing one or more tool response models where each response model predicts a measurement log based on a formation description, at least one of said models comprising a wetness parameter for that fraction of the characteristic volume of adsorbed water in a given mineralogy component, which is proportional to the volume Vclay of that component; a processor operatively connected with said first and second memories, performing constrained optimization of the formation description parameters based on a comparison of measurement log data in said first memory and tool response data in said second memory; the processor providing humanly readable output indicia of petrophysical properties of the geologic formation based on the models and the performed constrained optimization.

BRIEF DESCRIPTION OF THE DRAWINGS

FIG. 3 illustrates the adsorption isotherms constructed for both Ca- and Na-montmorillonites; FIG. 3A illustrates data concerning quantities of water adsorbed by these clays upon hydration by vapors obtained by different sources;

FIG. 4 illustrates $T_2$ distributions Ca-montmorillonite hydrated by water vapors; FIG. 5 is the corresponding distribution for Na-montmorillonite; FIG. 6 illustrates $T_2$ distributions from brine-saturated Ca-montmorillonite; FIG. 7 is the corresponding distribution for Na-montmorillonite;

DETAILED DESCRIPTION OF THE PREFERRED EMBODIMENTS

NMR Characterization of the Water Adsorbed by Clays

Hydration of Clays

Understanding the mechanism of water retention by clays is essential in modeling the petrophysical parameters for these clays. The clay-water interface has been studied extensively during the last 50 years by clay researchers from agronomy, soil science and geology. Excellent reviews on many aspects of the clay-water interactions are available, for example, from Van Olphen (1965), Grim (1968), Prost (1976), Sposito and Prost (1982), Low (1980), Guven (1992) and Prost et.al.(1998), which publications are incorporated by reference for background. Pertinent aspects of the hydration of an important class of clays, the smectide group which includes montmorillonite, are summarized below.

Figure 1:
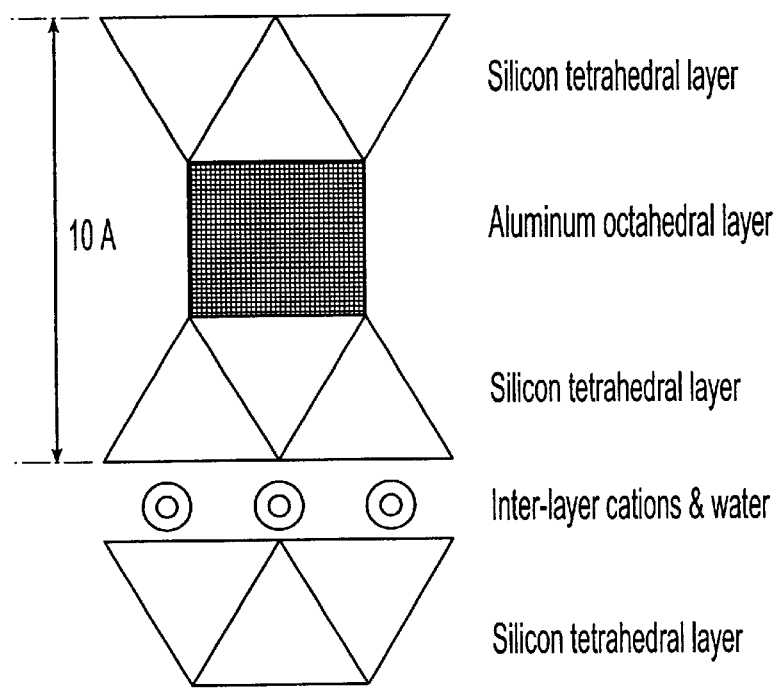
FIG. 1 is a schematic diagram of the structure of montmorillonite, which belongs to the smectite group of clay materials.
Figure 2:
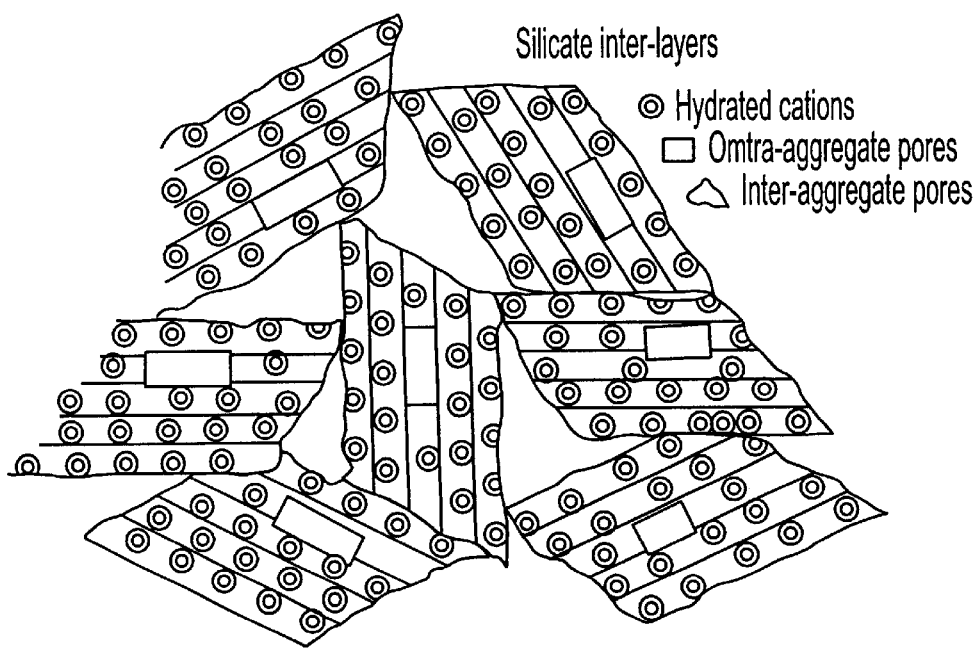
FIG. 2 depicts the surface of hydrated aggregates of montmorillonite, wherein the water is present in the interlayers, the intra-aggregate pores and the inter-aggregate pores in the wet clay fabric.

Water associated with clays has two components: water that is adsorbed on the clay surface, and water that occupies the inter-aggregate clay pores. The adsorbed water is either coordinated to the exchangeable cations—that are known as hydrophilic sites—or it is physiosorbed on the montmorillonite surface (Johnston et. al. 1992). The water bound to cations is more tightly held than that hydrating the "surface." The surface of montmorillonite has two components: internal—also called the interlamellar space—and the external surface. The clay also contains intra- and inter-aggregate pores. FIG. 1 is a schematic diagram of the structure of montmorillonite, showing the internal geometry of the tetrahedral and octahedral silicate layers and the interlayer water. FIG. 2 depicts the surface of hydrated aggregates of montmorillonite, wherein the water is present in the interlayers (interlamellar surface), the intra-aggregate pores and the inter-aggregate pores in the wet clay fabric. The hydration of montmorillonite, either by vapors or by water saturation, proceeds simultaneously on the internal and external surface and in the pores associated with the montmorillonite aggregates (Berend et. al. 1995, Prost et. al. 1998). At all stages of hydration the amount of adsorbed water on the internal surface exceeds the adsorbed water on the external surface. It is known that clays other than smectites generally do not have an internal surface, but they posses an external surface.

Montmorillonite belongs to the smectite group of clay minerals that are also known as swelling clays. Adsorption creates pillars between the clay layers and a water film on the external surface area of both particles and aggregates, which induces increases in spacing between the montmorillonite layers and in the distance between particles and aggregates, which is known as swelling. Essentially the swelling is due to multilayer adsorption even at very high water saturations. This type of adsorption occurs on the pre-existing water film on the hydrated exchangeable cations. Spectroscopic evidence (e.g., IR) supports the existence of two kinds of water molecules: one hydrating the cation and the other adsorbed on the surface covered by the hydrated cation. See Prost et. al., (1998). Sodium montmorillonite swells much more than any other variety, including Ca montmorillonites, because of the extremely hydrophilic nature of the Na cation and due to its small surface charge density. Also, the larger Na ion solvates with fewer water molecules than the smaller Ca ion. Fully hydrated Ca montmorillonite typically consists of 4 to 7 water interlayers. The Na-variety hydrated by salt water resembles the fully hydrated Ca-variety.

In water-saturated montmorillonite a diffusional exchange exists between the water on external surface and the water occupying the pores in the wet clay fabric. This type of hydration is inversely proportional to the square root of the salinity of the solution (thus fresh water produces maximum swelling). The hydrophilic nature of the Na ion is such that upon saturation by fresh water, the Na-montmorillonite could dissociate into individual silicate layers. These layers can be separated by distances of several microns. The hydration complexes between these layers consist of continuous diffused overlapping double layers. In an extreme case, the water in such clay resembles a uniform, continuous liquid.

The relevance of the mechanisms of montmorillonite hydration for the NMR analysis is apparent. The geometry of the space occupied by water of hydration is different for the adsorbed water on the clay surface from the water in the inter-aggregate clay pores. This is the underlying reason for the observed distinct NMR signatures corresponding to the two different types of spaces. In the case of hydration by water vapors, which produces clay containing only adsorbed water, the simplest $T_2$ distribution has a single narrow mode that shifts to slower decay times with increasing volume of adsorbed water. When the adsorbed water coexists with the pore-water, as in the case of water-saturated montmorillonites, the two forms of water generally relax separately, and the corresponding $T_2$ distribution is bi-modal. A third case may exist in which there is diffusional coupling, and the physics of interaction between the water types is more complicated. In particular, in certain cases such as clay super-saturated with fresh water, the diffusional coupling could be so pronounced that the $T_2$ distribution becomes uni-modal and is controlled by the size of the larger pores.

Experimental Procedures

Montmorillonite samples provided by The Clay Minerals Society have been used for the experiments reported herein. Montmorillonite is ideally suited for the purpose since it is known to hold a significant quantity of water, a property that makes this clay important not only for formation evaluation but also for other oilfield operations. In the experiments both Na- and Ca- varieties of montmorillonite were examined so as to build further on the experiments described in the prior art. Prammer et. al., (1996) and Matteson et. al. (1998). The objective was to establish the NMR response from the water adsorbed on the clay surface in the presence of the water occupying the inter-aggregate pores in the clays. However, in order to simplify the situation, it is first demonstrated that NMR detects the water adsorbed on the clay surface when no other form of water is present. This leads to the conclusion that the NMR porosity is a true total porosity. For clays that contain both adsorbed water and a volumetrically continuous water phase in the porosity of the clay aggregates the signal contains a component that can be ascribed to the adsorbed water and one associated with the remaining water.

Sample preparation is the key to the success of any experimental work on clays and in particular montmorillonite, because of its extremely hydrophilic nature. Gelling and/or clustering must be avoided by properly mixing the clay and water so that uniform hydration of the clay is achieved. In order to prepare montmorillonite samples containing only the clay-bound form of water, the clays were first humidified by water vapors using methods based on those in the hydration experiments reported by Mooney et. al., (1952); and Prost et. al., (1998). Next, the montmorillonites were hydrated by liquid water so as to prepare samples containing water in the inter-aggregate clay pores as well as the water adsorbed on the clay surface. The main goal of hydration was to gradually increase the water content of the montmorillonite while obtaining NMR $T_2$ distributions at every stage of hydration.

Hydration by water vapors was achieved by humidifying measured quantities of Ca- and Na-montmorillonites in a controlled humidity oven at relative humidities (RH) ranging from 40%–100%. Temperature was maintained between 39°–41° C. inside the humidifier. Samples humidified to stable weights at each level of RH were then transferred into clean glass vials and sealed to prevent any moisture losses. Hydration of montmorillonite by liquid water can be achieved by preparing pastes and slurries of measured quantities of room dried clay samples using brines of known salinity as well as fresh water. Fresh water may be necessary in order to tie the results of vaporization with water-saturation. The main objective of water-saturation was to achieve uniform hydration using the minimum appropriate quantity of water. The clay and water were mixed over a range of relative proportions (1:1 to 1:3.5) so as to systematically vary the degree of hydration of the samples analyzed later by NMR. Significant differences with respect to the achievable clay water ratios were observed during hydration of Ca- versus Na-montmorillonites. Na-montmorillonite could be uniformly hydrated at ratios of less than 1 (clay): 3.5 (water) only by using 50000 ppm and 100000 ppm brines. In the case of Ca-montmorillonite uniform hydration by both fresh water and brines was achieved at gradually increasing water contents starting at a clay:water ratio of 1:1. One sample of water-saturated Ca montmorillonite was also pressure squeezed at 2500 psi to achieve a clay:water ratio of greater than 1.

NMR responses were obtained from montmorillonite samples at various stages of hydration by means of a 1 MHz Coro Spec relaxometer at an inter-echo (TE) spacing of 0.3 ms. Echo trains gathered from each sample were processed by a multi-exponential decay inversion algorithm- MAP to obtain $T_2$ distributions, as described for example in U.S. Pat. No. 5,517,115, which is incorporated herein by reference. Moisture-stability in the hydrated montmorillonites was closely monitored by recording the sample weights before and after the NMR experiments. Upon completion of the NMR experiments samples were dried off to constant weights in an oven at 95° C. with zero humidity. Final dry weights were recorded for each sample and adsorption isotherms were constructed for the two montmorillonites.

NMR Results and Observations

FIG. 3 illustrates the adsorption isotherms constructed for both the Ca- and Na-montmorillonites. The table in FIG. 3A illustrates prior art reports concerning quantities of water adsorbed by these clays upon hydration by vapors. As clear from the illustration in FIG. 3, the NMR analysis results obtained in accordance with this invention are generally in agreement with the published data, confirming the applicability of NMR methods for this purpose. The reported amount of water adsorbed on Ca-montmorillonite ranges between 250–400 mg/g of dry clay, while the corresponding range for Na-montmorillonite is 198–400 mg/g. One or more of the following factors could be responsible for the large spread in the amount of water of hydration reported by different sources include variations in the quantity and type of sample used (natural clay powders versus synthetic films of clay), ability of the humidification equipment to maintain low-temperatures constant, the natural heterogeneity in the clay itself (compositional and textural differences), the duration of the humidification (months of humidification versus a few days) and others.

Figure 4:
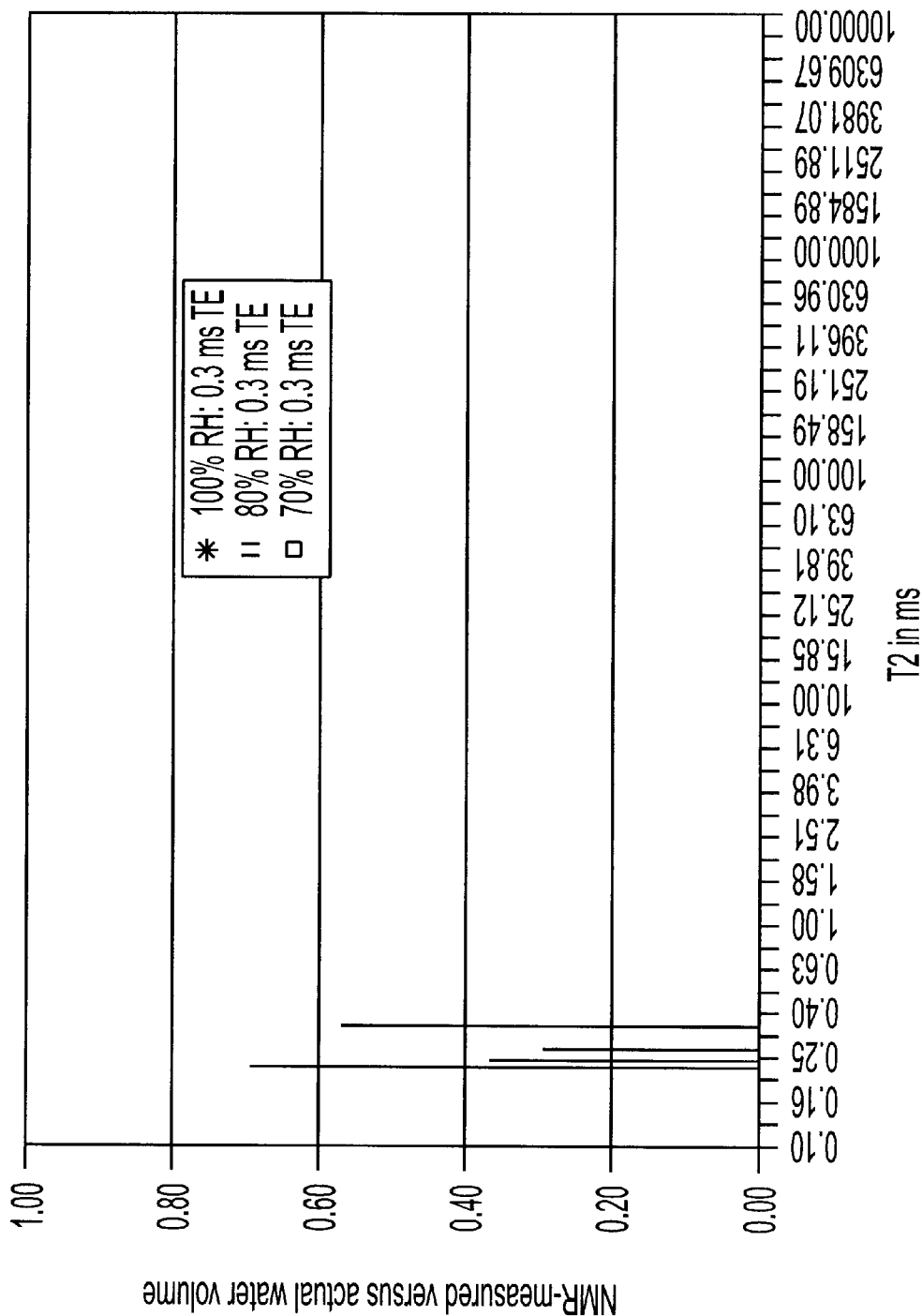
FIGS. 4–7 illustrate NMR $T_2$ distributions obtained in accordance with this invention from Ca- and Na-montmorillonites as hydrated by water vapors, fresh water and brines.
Figure 5:
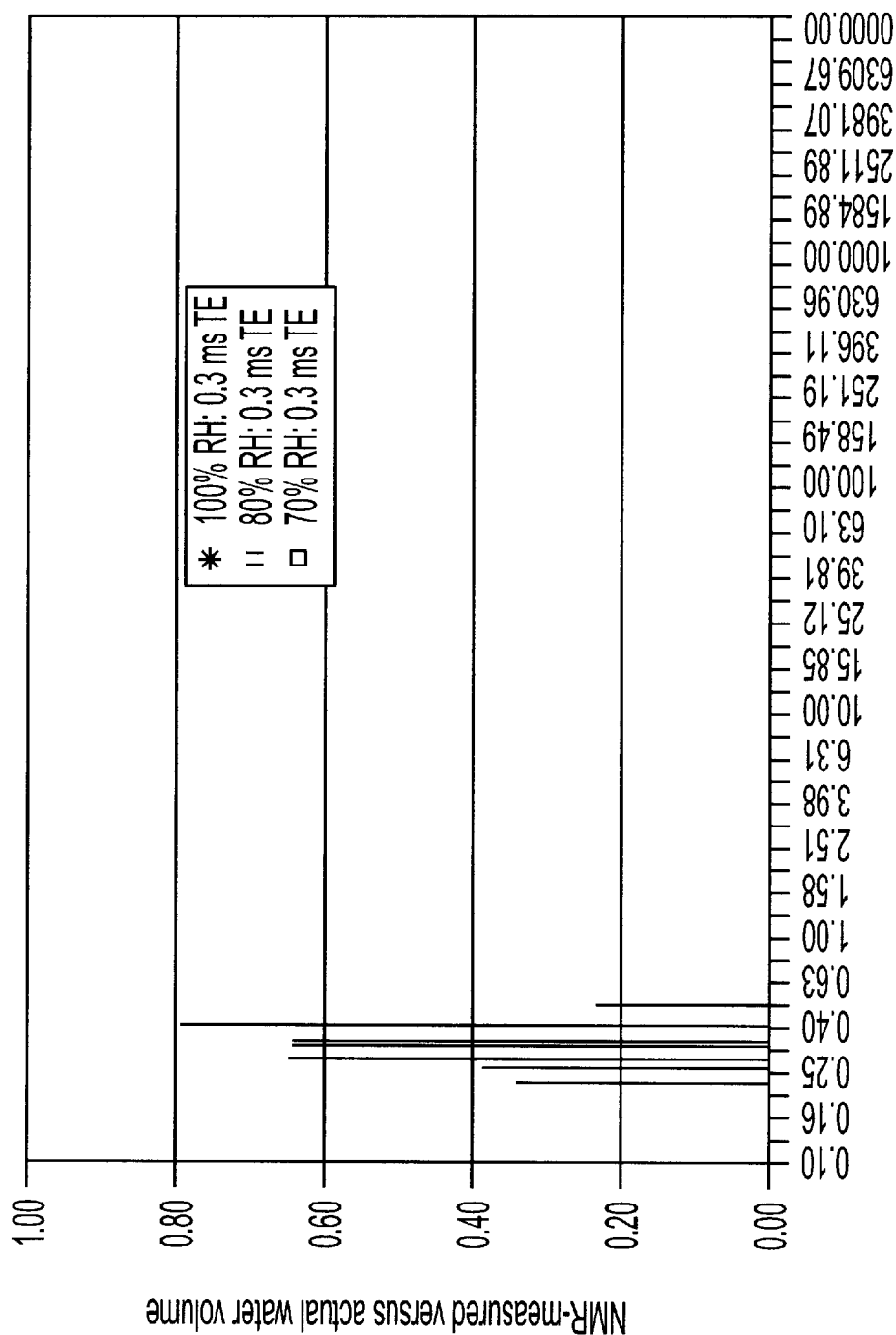
Figure 6:
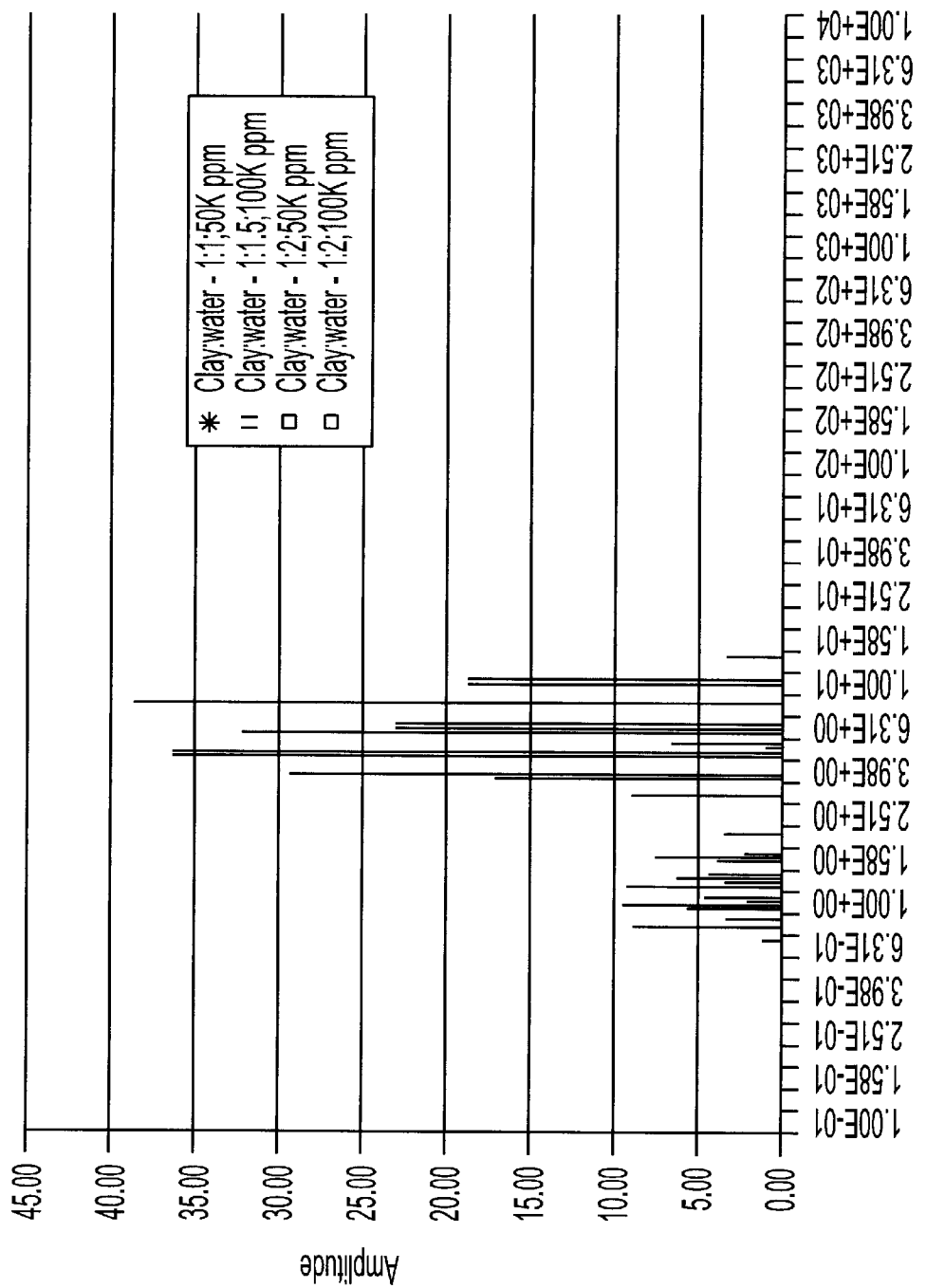
Figure 7:
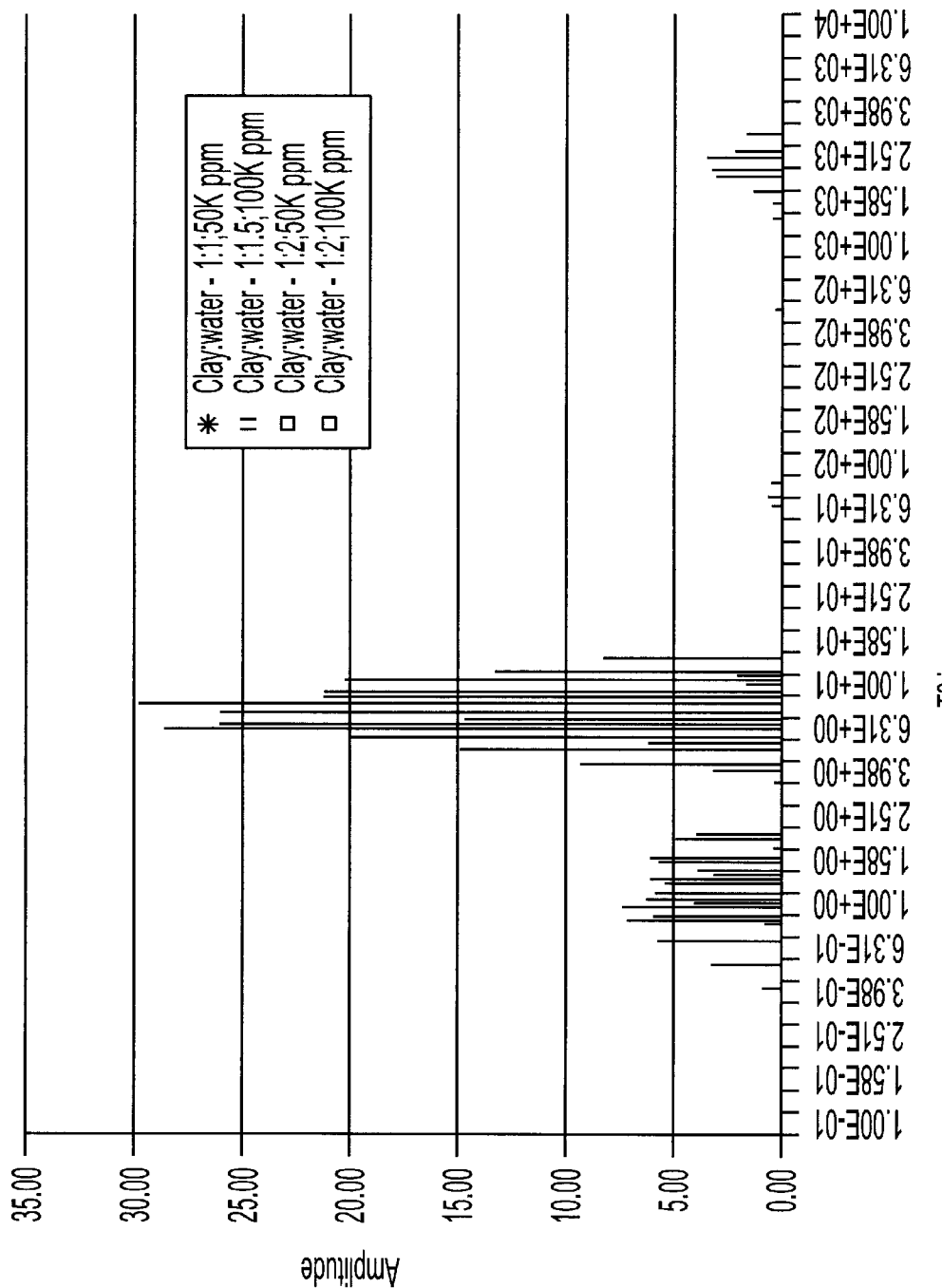
Figure 8:
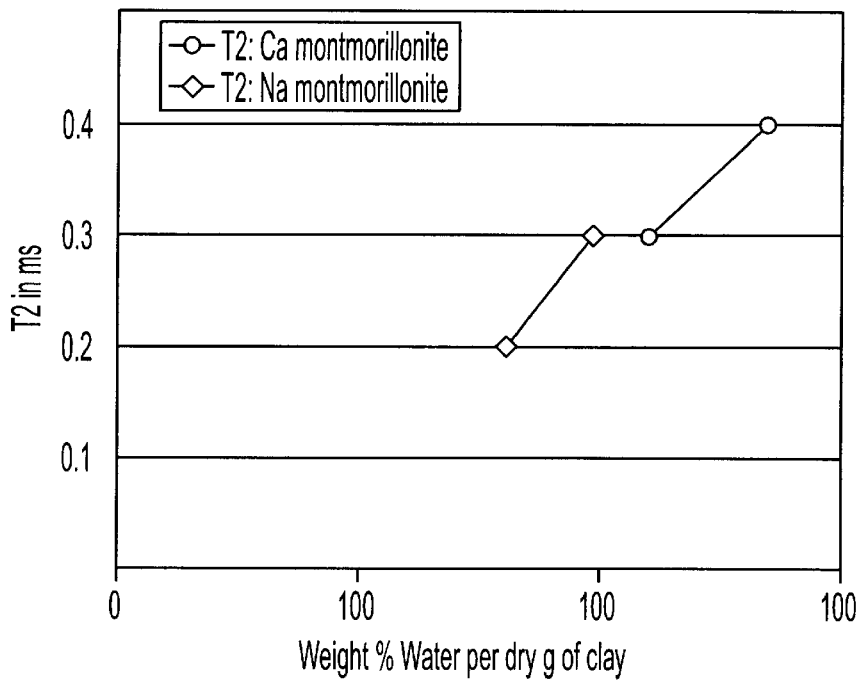
FIG. 8 illustrates the linear relationship between $T_2$ distributions of Ca-montmorillonite and Na-montmorillonite hydrated by water vapors from the water content.
Figure 9:
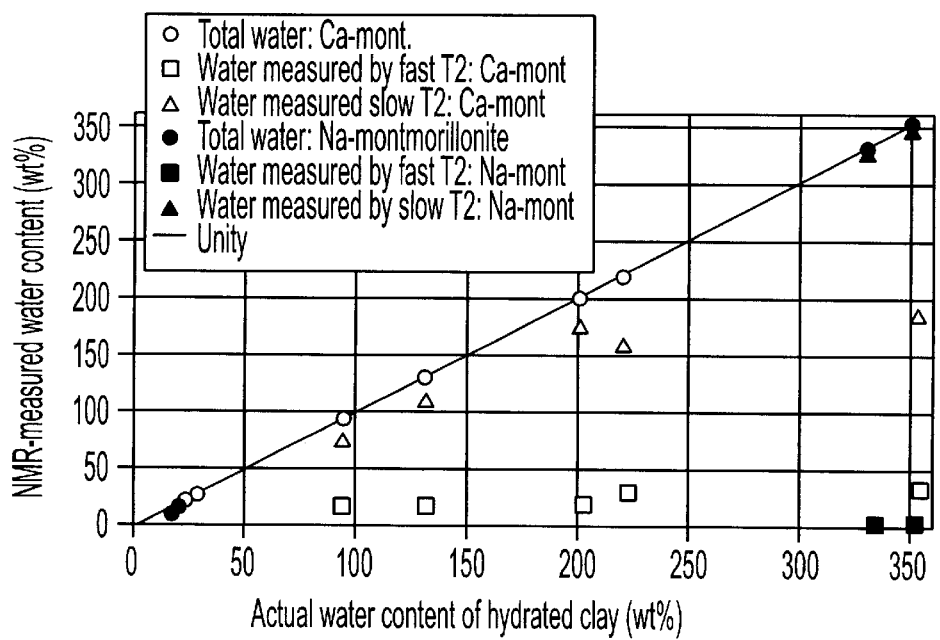
FIG. 9 is a comparison of actual versus NMR-measured volume of water of hydration in Ca- and Na-montmorillonites.

FIGS. 4–7 present the NMR $T_2$ distributions obtained in accordance with this invention from Ca- and Na-montmorillonites as hydrated by water vapors, fresh water and brines. As discussed above, the $T_2$ distributions obtained from the clay humidified by water vapors is unimodal, while it is bi-modal for the water-saturated clays. It can also be seen that the $T_2$ relaxation becomes progressively longer as the absolute water content of the montmorillonite increases. In particular, FIG. 4 illustrates $T_2$ distributions Ca-montmorillonite hydrated by water vapors; FIG. 5 is the corresponding distribution for Na-montmorillonite; FIG. 6 illustrates $T_2$ distributions from brine-saturated Ca-montmorillonite; FIG. 7 is the corresponding distribution for Na-montmorillonite. FIG. 8 illustrates the linear relationship between the $T_2$ relaxation time in ms, and the volume of water for the vapor hydration experiments. The $T_2$ distributions obtained from the clays saturated with liquid water are bi-model with the faster $T_2$ mode remaining at a fixed position clustering around 1 ms, while the slower $T_2$ component moves to slower relaxation times as the water content increases. As illustrated in FIG. 9, the linear correlation between the peak of the $T_2$ distribution and the volume of water holds for the slower $T_2$ mode.

In particular, FIG. 9 shows a comparison of NMR-measured water from each $T_2$ mode versus the actual water of hydration in accordance with the present invention. The figure illustrates the good match between the actual water content of the variously hydrated clays with the NMR-measured water content. This close correspondence, which is an aspect of the present invention, establishes a basis for using the NMR measurement as a total porosity log in formation evaluation. In the case of montmorillonites containing only the adsorbed water on the clay surface, the NMR-measured volume of water matches the actual water content when the amount of water of hydration exceeds 200 mg/g. It appears that below such water content the surfacially adsorbed water relaxes too fast to be fully recovered in the NMR $T_2$ distribution at a TE of 0.3 ms. In the case of the water-saturated clay, the NMR-measured total volume of water exceeds the liquid volume computed from summation of the fast and slow $T_2$ modes when the clay is super-saturated with water, i.e., when more water is available in the system than that required to completely saturate the clay surface as well as to fill up the inter-aggregate pores.

Figure 10:
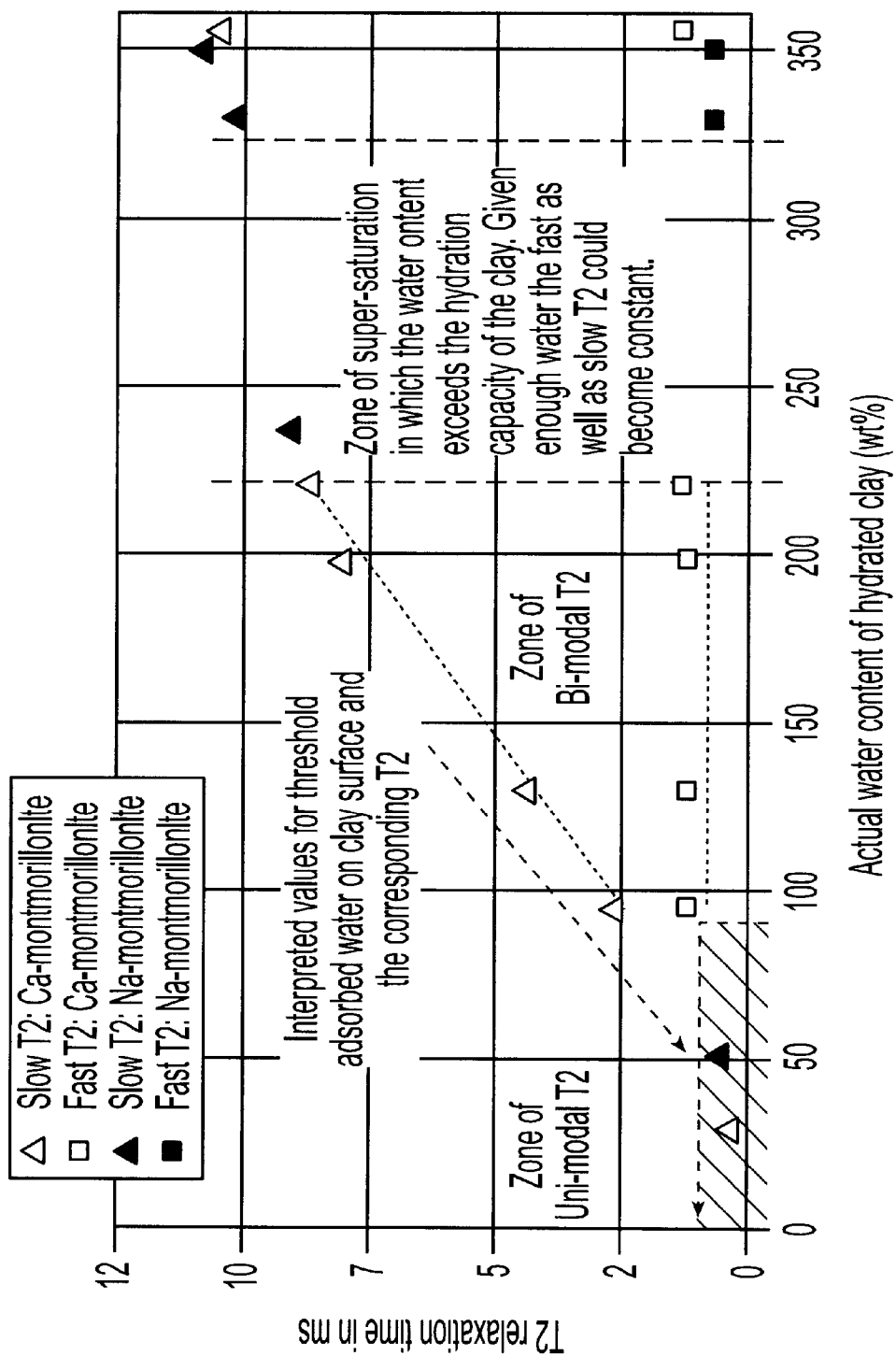
FIG. 10 is a diagram illustrating a comparison of $T_{23}$ versus NMR-measured volume of water in hydrated Ca- and Na-montmorillonites.

FIG. 10 is an interpretation of the hydration and $T_2$ data constructed in accordance with another aspect of the present invention. In particular, the trends of NMR $T_2$ distributions in FIGS. 4–9 suggest that the movement of the single $T_2$ mode (characteristic of the adsorbed water on clay surface)

to progressively slower times has a limiting threshold water content. Beyond this threshold the $T_2$ appears to bifurcate producing a bi-modal $T_2$ spectrum. Accordingly, in another aspect of the invention it is postulated (based upon the previous discussion of the clay-water interface) that such a threshold water content corresponds with maximum adsorption of water on the clay surface, after which any incremental water of hydration must enter the inter-aggregate clay pores that grow larger as the water content increases. It follows that this threshold water content defines the boundary between adsorbed water on clay surface and the water occupying the inter-aggregate clay pores.

The comparison of the hydration data with the NMR data shown in FIG. 10 shows that this boundary lies between about 270 mg/g and 1000 mg/g. Data from high-resolution electron optical investigations and spectroscopic measurements provide more precise limits on this value. It has been shown (Touret et al., 1990) that the apparent absolute content of water on the internal surface of montmorillonites ranges from 511 mg/g to about 450 mg/g corresponding respectively with water:dry clay ratios of 1.5 g/g and 2 g/g. That is, the minimum water adsorbed on the surface of water-saturated montmorillonites is about 450 mg/g. An optimum value for the threshold water adsorbed on the clay surface must additionally include the water on the external surface as well. Values ranging between 35 to 75 mg/g for the water held on external surface of montmorillonite have been reported in the prior art, (see Berend et. al., 1995). Thus, based on the above and further reference to FIG. 10, the value for the water adsorbed on the clay surface is estimated to be around 500 mg per dry gram of montmorillonite. Resolution of the clay-bound fraction of water-bearing rocks is important when the water exists as both clay-bound and discrete water phase in pores. Therefore, the above optimization of the adsorbed water on the surface of montmorillonite is useful in characterizing various petrophysical properties of the shales and reservoir rocks.

Considering the geometry of the pore space occupied by the above two types of water, it is apparent that the faster $T_2$ cluster around 1 ms in the bi-modal distribution illustrated in FIG. 10 is a measure of the adsorbed water, while the slower $T_2$ corresponds to the water in the porosity of the clay aggregates. Although, the faster $T_2$ at around 1 ms seems to be characteristic of the adsorbed water on the clay surface, the NMR-measured volume of water from this faster $T_2$ is significantly less than the value of 500 mg/g discussed above. Also, it is less than the amount of water adsorbed in hydration by vapors. A possible explanation is that a portion of the adsorbed water is in diffusional equilibrium with the pore-water. The process of hydration proceeds by multilayer adsorption in which the outer layers of water form on the previously formed films of water around the exchangeable cations. The outer layers are less tightly bound than the primary hydration shell. Therefore, it appears that the faster fixed $T_2$ observed in accordance with the present invention is a measure of the primary hydration shells of the ions, such as Na and Ca. These tightly bound water molecules are unable to take part in the diffusion exchange with the water in the larger inter-aggregate pores. The outer hydration shells, which are more mobile, apparently take part in the exchange. An extreme case of such diffusional exchange is due to the Na-montmorillonite saturated with fresh water. It yields a bi-modal $T_2$ spectrum, as shown in FIG. 4, in which the slower $T_2$ accounts for almost all of the total water. In such hydrated clays the dispersion of the montmorillonite is apparently almost complete, so as to produce a single continuous water phase.

Based on the above NMR characteristics of hydrated clays, suchs as the montmorillonites, the threshold maximum water adsorbed on the clay surface is defined in accordance with the present invention as the minimum proportion of adsorbed water in a given wet clay corresponding to which the NMR $T_2$ distribution is bi-modal. A direct test of this was not possible as it was not possible to physically prepare uniformly hydrated montmorillonite samples at any level close to 500 mg water/dry g of clay owing to the gelling nature of the clay and its tendency to form clusters when immersed in water.

Differentiation Between Adsorbed Water and Interstitial-pore Water

It is clear from the above discussion of the clay-water interface that the oft-repeated petrophysical term "clay-bound water" refers to the water of hydration that is adsorbed on the clay surface. Porosity log responses, such as NMR, density and neutron, provide a measure of the total water present in the pore space of the subsurface rocks, which includes both the clay-bound and the interstitial pore water. In this respect NMR measurements are unique because they not only provide a measure of total water content (i.e., porosity) but also capture information useful to characterize the changes in the geometry of the pore space occupied by water.

As known, the relaxation of water in porous media is related to the volume-surface ratio of the pore space occupied by water. As such, the $T_2$ characteristic of the clay-bound water is distinct from that of the interstitial pore water. FIGS. 4–10 illustrate that the NMR $T_2$ distributions from water-saturated montmorillonites are bi-modal because they represent water relaxing in pore spaces with two different geometries. Faster $T_2$ times that cluster around 1 ms are a measure of the water in the inner hydration shells of exchangeable cations in the interlamellar space of montmorillonites. The $T_2$ times slower than 1 ms, on the other hand, represent water relaxing in the inter-aggregate pores of the water-saturated clays. It has also been demonstrated that the $T_2$ distribution is uni-modal in the case of montmorillonite hydrated by water vapors, which contains only the adsorbed water. Here, the T2 is linearly related to the volume of water of hydration in accordance with the simple relationship $$1/T2 = pS/V.$$

Figure 11:
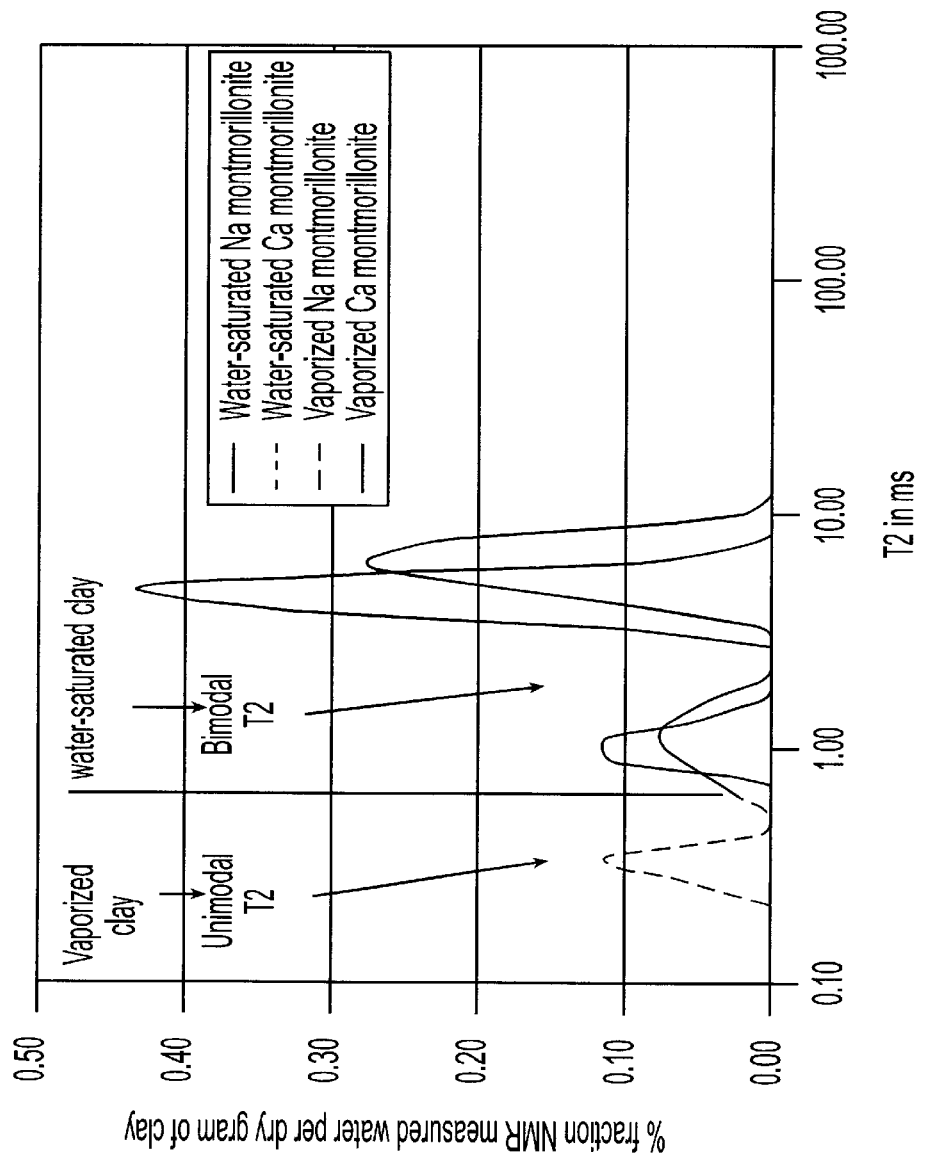
FIGS. 11 and 12 illustrate typical $T_2$ distributions obtained in accordance with this invention from water-wet montmorillonites.

FIG. 11 displays typical $T_2$ distributions obtained from water-wet montmorillonites. With reference to FIG. 2, as the water of hydration increases gradually, the surface of montmorillonite (both internal and external) becomes fully saturated and any additional water occupies the interstitial pores that grow in size upon further addition of water. This is evident also in the $T_2$ characteristics, illustrated in FIG. 12. The faster $T_2$ that is a measure of the adsorbed water remains fixed, while the mode of the slower $T_2$ moves to longer times. Thus, NMR shows a new method of diagnosing the boundary between adsorbed- and interstitial water.

Figure 12:
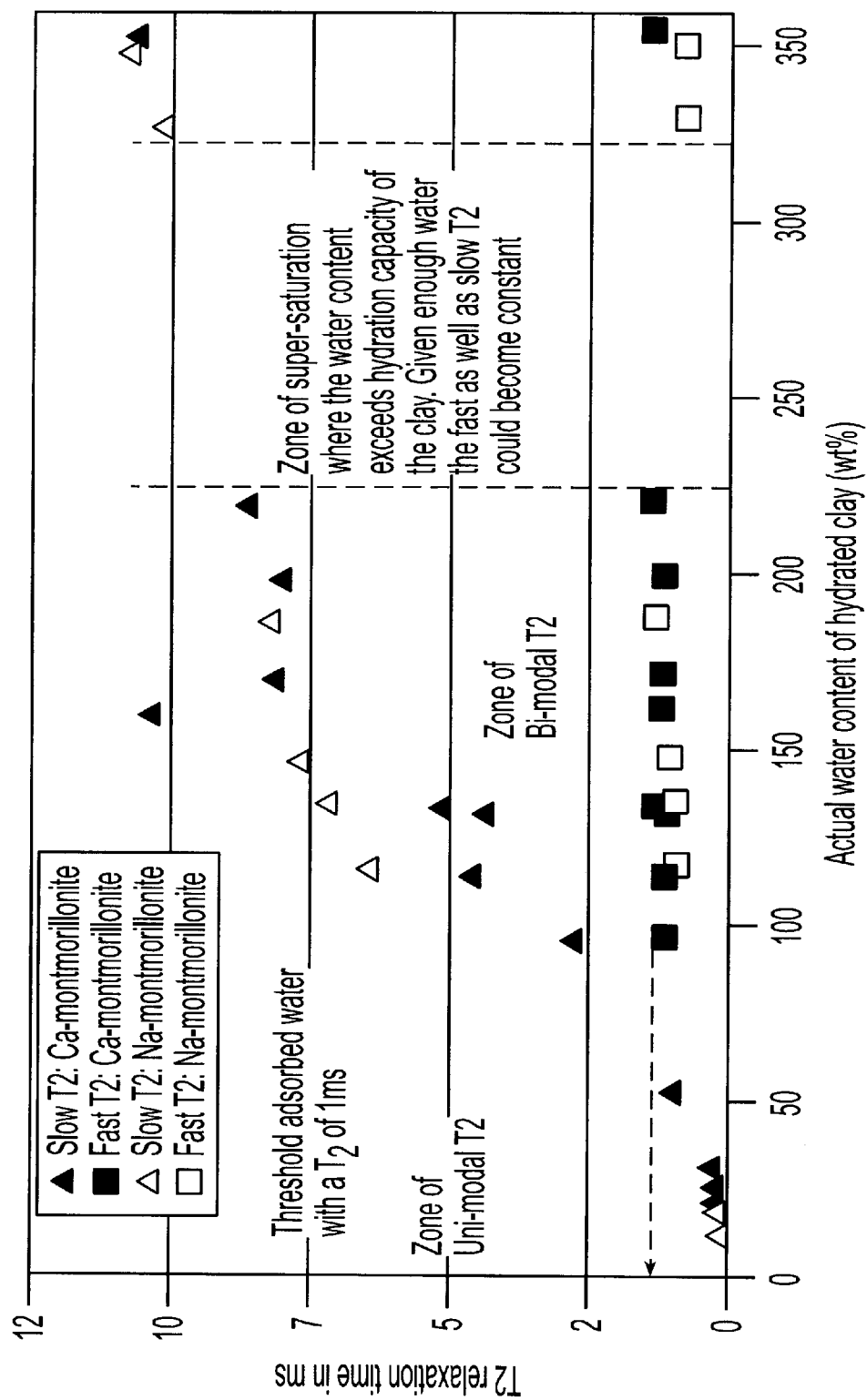

Although it is difficult to measure directly, the threshold for the adsorbed water in montmorillonite has been interpreted to be 500 mg per gram of dry clay based upon the $T_2$ characteristics of the hydrated clay illustrated in FIG. 12. Direct measurements are complicated because of difficulties associated in providing uniform hydration of the clay at a ratio of less than 1 (clay):1(water). High resolution electron optical and IR spectroscopic characterization of the internal surface of montmorillonite (Touret et. al., 1990) combined with the analysis of water present on the clay's external surface (Berend et. al., 1996) also support the above-interpreted amount of 500 mg/g for the threshold clay-bound water in montmorillonite. The dry clay densities of the montmorillonites were found to range between 2.6–2.7 g/cc. Simple volumetric considerations show that the above threshold corresponds to the ratio of the adsorbed water volume divided by the wet clay volume of 0.57. This ratio is hereafter defined as "wetness"—i.e., wetness for montmorillonite (or wetness-clay when used generically for any clay mineral), which is intrinsic to each clay. The term "wetness_clay" (different from clay porosity) is proposed as to emphasize that the adsorbed water occupies the surface of montmorillonite, a space distinct from the conventionally understood interstitial pores.

In this regard, it is natural to inquire about whether the threshold adsorbed water content and the resultant wetness-clay are applicable to subsurface rocks. In accordance with this invention, it is believed that they are for the following reasons. The hydration experiments and NMR characterization described above deal with montmorillonites fully saturated with water. Thus, it is only required to demonstrate that under the subsurface conditions the threshold adsorbed water content does not decrease for a montmorillonite.

In a subsurface formation containing montmorillonite as the only clay mineral the total water in the pore space can be regarded as a mixture of two components: one that fills the interstitial pores and the other bound to the surface of montmorillonite that can either be detrital or authigenic. The interstitial pore water component is not an issue since one is only concerned with the threshold clay-bound water. The factors that are commonly known to affect the water content of the subsurface clays are overburden pressure, temperature and salinity of formation water. Recent hydration and NMR experiments were conducted under different pressure and salinity. It was observed that even at 10000 psi and a salinity of 100000 ppm the absolute water content of a uniformly hydrated montmorilonite could not be lowered below 1000 mg per dry g of clay. This is considerably greater than the above-described threshold for the adsorbed water. Thus, increasing the pressure or salinity can not significantly reduce the threshold amount of adsorbed water occupying the internal and external surface of montmorillonite. This appears logical since the "surface" of montmorillonite can not support "overburden". Changes in the formation water salinity would not alter the threshold amount of adsorbed water because the increased concentration of salt only restricts the "swelling" of montmorillonite and not the adsorption process. Therefore, it is believed that the threshold-adsorbed water is an intrinsic property of the montmorillonite clay. Reduction in the threshold content of adsorbed water on montmorillonite surface implies a mineralogical change.

Implications for Porosity Log Analysis

The wetness of 0.57 computed above from the threshold adsorbed water content in montmorillonite is regarded as an intrinsic petrophysical property. It is apparent that the wetness and volume of montmorillonite in a rock are directly linked. The former must gradually decrease with the latter. They both are linked to the threshold adsorbed water by the relationship: Wetness=Adsorbed water volume/Volume of wet clay. The total porosity is a volumetric summation of the adsorbed water and the interstitial pore water. It should be noted that wetness refers only to the adsorbed water bound to the clay surface. As such, it does not include the water that could be trapped within the clay aggregates. In the case of a shaly sand core the porosity of the detrital as well as authigenic clay aggregates has been shown to hold bound water in substantial amounts. Although this water is bound in the sense that it can not be produced (pore sizes between 1–10 microns), it is not "clay-bound". The obvious implication is that clay-free porosity can not be regarded to be an effective porosity for hydrocarbon production since it always includes very small interstitial pores trapped within clay aggregates.

The threshold value of 500 mg/g for the adsorbed water computed ni accordance with the present invention translates to a density of 1.7 g/cc for montmorillonite considering that the dry clay density ranges between 2.6–2.7 g/cc. Therefore, assuming a sandstone matrix grain density of 2.65 g/cc the wet-montmorillonite that has a density of 1.7 g/cc will possess an apparent density-porosity of 58%. Hence, in the case of subsurface logs recorded against a shaly sandstone containing montmorillonite, assuming that there are no other constraints (e.g., mud filtrate density, other minerals or fluids etc), the wet-clay-density-porosity parameter should be 58 %.

It should be noted that the wetness of 0.57 and density log porosity of 58% account only for adsorbed water (and not hydroxyls) in montmorillonite. Thermal neutron logs are known to respond to both water and the hydroxyls in the clay structure. Thus, for a wet montmorillonite clay the neutron porosity should equal the sum of density-porosity and the dry clay neutron porosity. The published values for dry clay neutron porosity for montmorillonites center around 12% (Ellis et. al., 1994, Chart Books Halliburton, 1991 & Schlumberger, 1994). Thus, the wet-montmorillonite-porosity for a neutron log should be 70%. These refined parameter-values of 58% (density porosity) and 70% (thermal neutron) are recommended to be used in cross plots, overlays and any porosity models used for shaly sand evaluation.

Clay Typing Using NMR-based Models

The experimental work on hydrated clays discussed above illustrates that the adsorbed water on the internal and external surfaces of the claim minerals is fully represented in the NMR $T_2$ distribution. In addition, NMR experiments were used to characterize the optimum volumes of surficially adsorbed water in common clay minerals. In the case of a shaly sandstone core, it was also shown that the NMR porosity computed as a summation of the $T_2$ distribution matches the helium porosity measured after drying the rocks at 100° C. Thus, the adsorbed water in clays is fully represented in the NMR porosity.

In another important aspect of the present invention, the NMR porosity of the clayey rocks can be modeled as having two components: one-due to the adsorbed water on clay surfaces (Phi_NMR_clay) and the other due to the bulk fluids occupying pores of all sizes (Phi_NMR_bulk). The component due to the adsorbed water Phi_NMR_clay attains its maximum threshold in the case of the water saturated pure clays and decreases gradually, being linearly proportional to the volume of claiy in a given rock.

As noted, in accordance with the present invention a new petrophysical parameter named "wetness clay" is proposed for that fraction of the characteristic volume of adsorbed water in a given clay mineral, which is proportional to the volume Vclay of that clay mineral. Thus, $$\text{wetness\_clay} = \text{Phi\_NMR\_clay} / \text{Vclay} \qquad \text{Eq. (1)}$$

It follows that wetness_clay equals Phi_NMR_clay in pure clays. In accordance with the present invention the above relationship can be used to model the NMR total porosity as PhiT_NMR=(wetness_clay*Vclay)+Phi_NMR_bulk   Eq. (2)

The porosity due to bulk volume Phi_NMR_bulk can also be separated into its volumetric components, matrix minerals and water, assuming respective wetness value of zero and unity. Thus, Phi_NMR_bulk=(wetness_matrix*Vmatrix)+(wetness water*Phie)   Eq. (3)

where Phie represents pores of all sizes containing water in bulk form.

It is known in the art that the NMR porosity is not independent of the rock mineralogy. In particular, it has a component that offers a measure of relative abundance of the clay type. In accordance with the present invention, the NMR porosity model expressed in Eq. (2) and Eq. (3), using the characteristic wetness values for various clay minerals is applied in a novel method of clay typing, preferably applied in shaly sand log analysis.

The new application of the wetness_clay parameter is based on constrained inversion of an overdetermined or at least completely determined log data set containing, in a specific embodiment, gamma (GR), bulk density (Rhob), thermal neutron (Nphi) and NMR logs. In a specific embodiment, the method assumes water saturated pores. As known in the art, the above logs have well defined linear responses proportional to the volumetric components of matrix minerals, clay minerals and pore fluids. Accordingly, if an estimate of the matrix and clay minerals volumes is available or can be derived, one can derive a generic log that accurately represents the contribution of different clay and matrix types. More specifically, in accordance with the present invention, $$LOG = \sum_{i=1}^{logs} \left( Vmat * LOGmat_i + \sum_{j=1}^{clay} Vcl_j * LOGcl_{ij} + Phie * LOG_i w \right)$$   Eq. (4)

where, the i-index runs over the different logs available, such as GR, Rhob, Nphi and NMR, and in a preferred embodiment the clay index j corresponds to a typical clayey sandstone consisting of quartz and other minerals and four common sedimentary clays: montmorillonite, illite, kaolinite and chlorite. The montmorillone component was considered in detail above. Similar relationships can be derived for the remaining three or other clay components used in different embodiments of the invention.

In accordance with the present invention, the available log data is processed with an initial set of assumptions in terms of the matrix and clay minerals. In a preferred embodiment the technique requires several iterations, so as to statistically minimize the errors.

Figure 13:
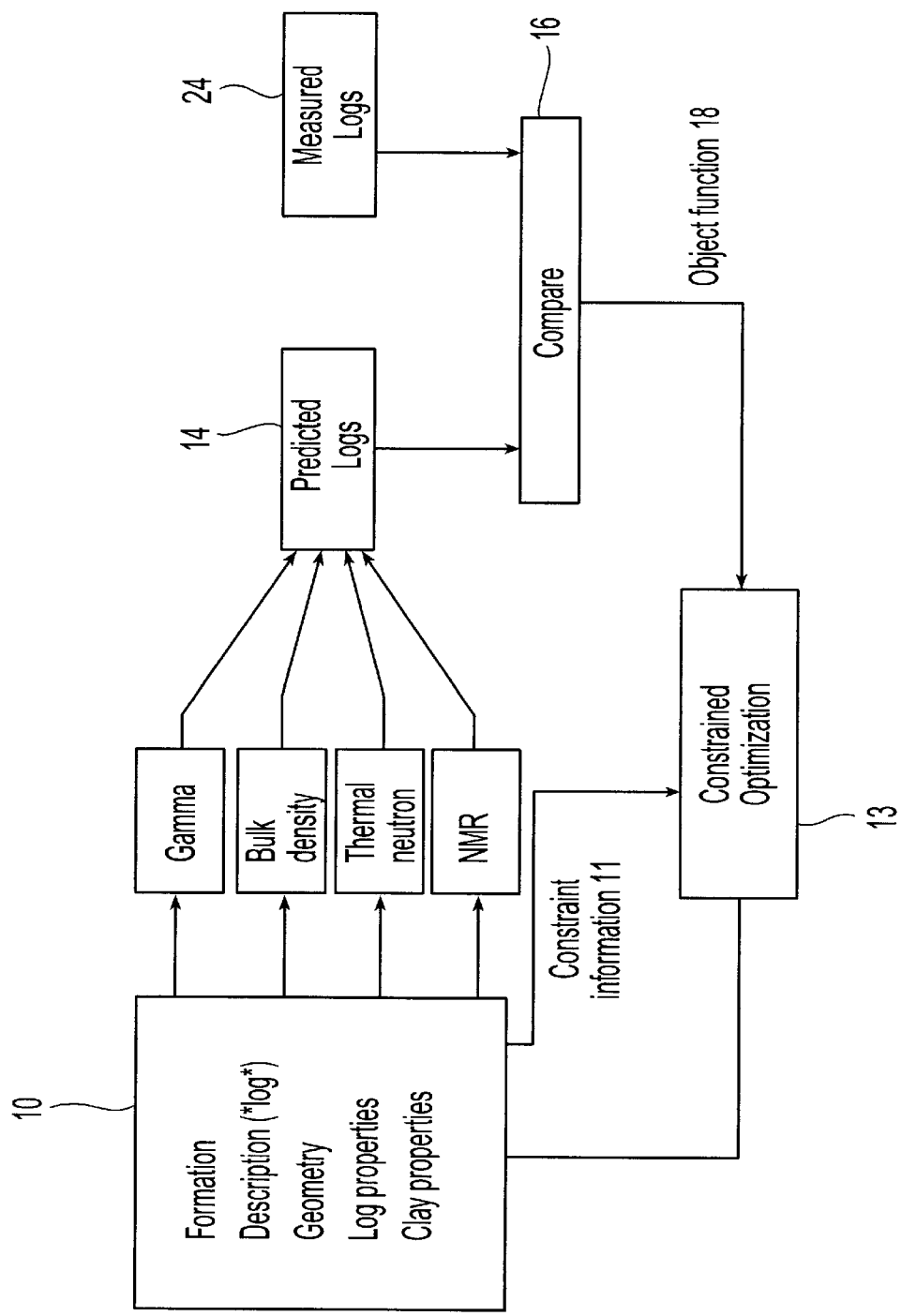
FIG. 13 is a block diagram illustrating the method of the present invention with the formation properties given in terms of different parameters.

FIG. 13 is a block diagram illustrating one embodiment of the system and method of the present invention for the characterization of the formation properties given in terms of different log and petrophysical parameters. In particular, as illustrated a formation description 10 is used as input into one or more tool response models 12. These models may be constructed for practically any type of tool, which with gamma (GR), bulk density (Rhob), thermal neutron (Nphi) and NMR tools being used in a preferred embodiment.

The predicted logs 14 are compared with the actual measured logs 24 in a comparison step 16. An object function 18 is defined, which is a function of the difference error obtained by comparing the predicted logs 14 and the measured 24. The object function indicates the accuracy and consistency of the formation description 10. Preferably, the object function 18 is combined with constraint information 11, which is typically available from prior measurements or is available from the literature. A constrained optimization algorithm 13 is used to compute a correction or adjustment to the formation description 10. The process of comparing the predicted logs 14 with the measured logs 24 is repeated until the object function reaches a predetermined value.

The object function 18 preferably is general and may, for example, be the weighted sum of several factors, including the Vclay parameters described above. Naturally, the most important contributing factor is the difference error between the predicted and measured logs. Preferably, the difference error from each logging tool may be weighted independently to account for different logging units (e.g., density in grams/cc versus velocity in ft/sec), the relative importance of the log, and the quality and noise levels in the logs.

Depending on the form of the object function, the constraints imposed, and variational knowledge of the models, this minimization involves an iterative process whereby the parameter estimates are successively refined until the error criterion of the object function is reduced to an acceptable level. Because, in general, the computed logs depend non-linearly on both of the formation geometric and property parameters, the best estimates are obtained using an iterative nonlinear optimization procedure. Various optimization routines are known in the art and will not be discussed in further detail.

The preferred method begins by specifying an initial set of formation geometry, property and other parameters, for example, layer boundaries. Beginning with this initial model, the procedure iteratively estimates the formation geometry and property parameters by comparing a number of actual log measurements with a number of predicted log measurements. The final formation representation, which minimizes the pre-set error criterion is selected as the best estimate of the unknown parameters. As known in the art, the parameters may also be constrained to satisfy auxiliary conditions, for example, to lie within a predetermined range of values, or for a set of values to sum to unity, in which case a constrained Gauss Newton optimization procedure may be used. Various optimization schemes are presented in the prior art. The reader is directed, for example, to the disclosure in U.S. Pat. No. 5,675,147, which is incorporated herein by reference, and the relevant disclosure in "Numerical Recipes: The Art of Scientific Computing," Cambridge University Press, 1986, which is incorporated for background.

While the invention has been described with reference to the preferred embodiments, it will be appreciated by those of ordinary skill in the art that modifications can be made to the structure and form of the invention without departing from its spirit and scope which is defined in the following claims.

What is claimed is:

1. A method for determining petrophysical properties of geologic formations containing clay materials, comprising:
   (a) providing a model of the geologic formation, said model comprising a wetness parameter for that fraction of the characteristic volume of adsorbed water in a given mineralogy component, which is proportional to the volume Vclay of that component;
   (b) providing log data corresponding to the geologic formation;
   (c) performing constrained inversion of the provided data log using the model of the geologic formation; and (d) determining petrophysical properties of geologic formations based on the provided model and the performed constrained inversion, wherein step (d) comprises determining a generic log of the formation according to:

$$LOG = \sum_{i=1}^{logs}\left(Vmat*LOGmat_i + \sum_{j=1}^{clay} Vcl_j*LOGcl_{ij} + phie*LOG_iw\right)$$

where, LOG is the generic log, the i-index runs over the different logs available, such as gamma, bulk density, thermal neutron and NMR; Vmat is the matrix volume; $Vcl_j$ is the volume of the j-th clay mineral and the clay index j corresponds to a typical clayey sandstone consisting of quartz and other minerals and common sedimentary clays, Phie represents pores of all sizes containing water in bulk form; LOGmat, $LOGcl_{ij}$ and $LOG_iw$ are the corresponding log parameters for the matrix, clay and bulk water respectively.

2. The method of claim 1 wherein the sedimentary clays are selected from the group of montmorillonite, illite, kaolinite and chlorite.

3. The method of claim 1, wherein step (a) further comprises providing one or more tool response models for tools used in step (b) to provide log data corresponding to the geologic formation.

4. An article of manufacture comprising a computer program, which when run on a computer determines a generic log of the formation according to the method in claim 1.

5. The method of claim 1, wherein the log data comprises at least NMR log data.

6. The method of claim 1, wherein the log data comprises NMR log data and at least one of the group of gamma (GR), bulk density (Rhob) and thermal neutron (Nphi) log data.

7. A method for determining petrophysical properties of geologic formations containing clay materials, comprising:
   (a) providing a model of the geologic formation, said model comprising a wetness parameter for that fraction of the characteristic volume of adsorbed water in a given mineralogy component, which is proportional to the volume Vclay of that component;
   (b) providing log data corresponding to the geologic formation;
   (c) performing constrained inversion of the provided data log using the model of the geologic formation; and
   (d) determining petrophysical properties of geologic formations based on the provided model and the performed constrained inversion,
   wherein the wetness clay parameter is defined as: wetness_clay=Phi_NMR_clay/Vclay.

8. The method of claim 7, wherein step (d) comprises determining the clay types present in the geologic formations.

9. The method of claim 7, wherein step (c) comprises comparing a model response to log data and computing a corresponding error function based on the comparison; minimizing the error function using an iterative process whereby formation parameter estimates in the provided model of the geologic formation are successively refined until the error function criterion is reduced to a predetermined level.

10. The method of claim 7, wherein step (b) comprises providing NMR log data, and wherein NMR porosity of the clay materials is modeled in step (a) as having one component due to adsorbed water on clay surfaces (Phi_NMR_clay) and a second component due to bulk fluids occupying pores of all sizes (Phi_NMR_bulk ).

11. The method of claim 7, wherein NMR porosity of clay materials is modeled (a) as PhiT_NMR=(wetness_clay*Vclay)+Phi_NMR_bulk where PhiT_NMR is the NMR porosity; wetness_clay is the wetness parameter; Vclay is the volume of the clay material; and PhiT_NMR_bulk is the component of NMR porosity due to bulk fluids occupying pores of all sizes.

12. The method of claim 11, wherein the Phi_NMR_bulk component further comprises a volumetric component (Vmatrix), a matrix minerals component (wetness_matrix), and a water component (wetness_water).

13. The method of claim 12, wherein the Phi_NMR_bulk component is further modeled as Phi_NMR_bulk=(wetness_matrix*Vmatrix)+(westness_water*Phie)

where Phie represents pores of all sizes containing water in bulk form.

14. The method of claim 7, wherein step (a) further comprises the step of computing predicted log information based on the model of the geologic formation.

15. The method of claim 14, further comprising the steps of
   (e) comparing the predicted log information with the provided log data; and
   (f) adjusting model of the geologic formation based on the comparison.

16. The method of claim 15, further comprising the step of
   (g) repeating steps (a)–(f) until a measure of the comparison reaches a predetermined value.

17. The method of claim 15, wherein step (e) further comprises the step of computing an error measure between the predicted log information and the provided log data.

18. The method of claim 17, wherein step (f) is performed by using a constrained optimization algorithm taking input from the error measure.

19. The method of claim 17, wherein step (e) further comprises the step of computing an error measure between the predicted log information and the provided log data for one or more different logging tools.

20. The method of claim 19, wherein the error is a weighted sum of one or more error measures for one or more different logging tools.

21. The method of claim 7, wherein the log data comprises at least NMR log data.

22. The method of claim 7, wherein the log data comprises NMR log data and at least one of the group of gamma (GR), bulk density (Rhob) and thermal neutron (Nphi) log data.

23. A method for determining petrophysical properties of geologic formations containing clay materials, comprising:
   (a) providing a model of the geologic formation, said model comprising a wetness parameter for that fraction of the characteristic volume of adsorbed water in a given mineralogy component, which is proportional to the volume Vclay of that component;
   (b) providing log data corresponding to the geologic formation;

(c) performing constrained inversion of the provided data log using the model of the geologic formation; and (d) determining petrophysical properties of geologic formations based on the provided model and the performed constrained inversion, wherein step (b) comprises providing NMR log data, and wherein NMR porosity of the clay materials is modeled in step (a) as having one component due to adsorbed water on clay surfaces (Phi_NMR_clay) and a second component due to bulk fluids occupying pores of all sizes (Phi_NMR_bulk), and wherein the component due to the adsorbed water Phi_NMR_clay attains a maximum in the case of the water saturated pure clays and is linearly proportional to the volume of clay in the formation.

24. The method of claim 23, wherein the log data comprises NMR log data and at least one of the group of gamma (GR), bulk density (Rhob) and thermal neutron (Nphi) log data.

25. A geological formation interpretation system comprising:

means for providing a model of a geologic formation, said model comprising a wetness parameter for that fraction of the characteristic volume of adsorbed water in a given mineralogy component, which is proportional to the volume Vclay of that component;

means for providing log data corresponding to the geologic formation;

processor means performing constrained inversion of the provided data log using the model of the geologic formation; and means for determining petrophysical properties of geologic formations based on the provided model and the performed constrained inversion, wherein the means for determining petrophysical properties comprises means for determining a generic log according to:

$$LOG = \sum_{i=1}^{logs} \left( Vmat * LOGmat_i + \sum_{j=1}^{clay} Vcl_j * LOGcl_{ij} + phie * LOG_i w \right)$$

where, LOG is the generic log, the i-index runs over the different logs available, such as gamma, bulk density, thermal neutron and NMR; Vmat is the matrix volume; $Vcl_j$ is the volume of the j-th clay mineral and the clay index j corresponds to a typical clayey sandstone consisting of quartz and other minerals and common sedimentary clays, Phie represents pores of all sizes containing water in bulk form; LOGmat, $LOGcl_{ij}$ and $LOG_i w$ are the corresponding log parameters for the matrix, clay and bulk water respectively.

26. The method of claim 25, wherein the means for providing log data comprises an NMR logging tool.

27. The system of claim 25, wherein the means for providing log data comprises an NMR logging tool and at least one of the group of: gamma, bulk density and thermal neutron tool.

* * * * *